US010923980B2

(12) United States Patent
Kokubo et al.

(10) Patent No.: US 10,923,980 B2
(45) Date of Patent: *Feb. 16, 2021

(54) MOTOR, ACTUATOR, AND MEDICAL SUPPORT ARM APPARATUS

(71) Applicant: SONY CORPORATION, Tokyo (JP)

(72) Inventors: Wataru Kokubo, Tokyo (JP); Yasuhisa Kamikawa, Tokyo (JP); Toshimitsu Tsuboi, Tokyo (JP); Yohei Kuroda, Tokyo (JP); Jun Arai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 126 days.

This patent is subject to a terminal disclaimer.

(21) Appl. No.: 16/119,265

(22) Filed: Aug. 31, 2018

(65) Prior Publication Data
US 2019/0036407 A1 Jan. 31, 2019

Related U.S. Application Data

(63) Continuation of application No. 15/121,466, filed as application No. PCT/JP2016/052982 on Feb. 2, 2016, now Pat. No. 10,128,714.

(30) Foreign Application Priority Data

Mar. 5, 2015 (JP) ................. 2015-043761

(51) Int. Cl.
H02K 3/34 (2006.01)
A61B 90/50 (2016.01)
(Continued)

(52) U.S. Cl.
CPC ............. *H02K 3/345* (2013.01); *A61B 34/74* (2016.02); *A61B 90/50* (2016.02); *H02K 3/34* (2013.01);
(Continued)

(58) Field of Classification Search
CPC .. A61C 1/00; A61C 1/06; A61B 17/00; A61B 17/16; A61B 17/161;
(Continued)

(56) References Cited

U.S. PATENT DOCUMENTS 4,862,024 A 8/1989 Stingle et al.
6,425,761 B1 7/2002 Eibofner
(Continued)

FOREIGN PATENT DOCUMENTS

CN 101076288 A 11/2007
CN 101227870 A 7/2008
(Continued)

OTHER PUBLICATIONS

John Bakes, "A Practical Guide to IEC 60601-1", Rigel Medical, Jun. 2007, pp. 1-22.
(Continued)

Primary Examiner — Tran N Nguyen
(74) Attorney, Agent, or Firm — Chip Law Group

(57) ABSTRACT

In order to realize a movable mechanism capable of being configured more compactly and also capable of ensuring higher safety. A motor is provided. Also, an electrically active part is provided with an insulating structure so that insulating properties between the electrically active part and one or more conductors near the electrically active part satisfy a certain safety standard regarding medical electrical equipment.

15 Claims, 10 Drawing Sheets

(51) Int. Cl.
*A61B 34/00* (2016.01)
*A61B 34/32* (2016.01)
*A61B 50/13* (2016.01)
*A61B 90/00* (2016.01)
*H02K 1/27* (2006.01)

(52) U.S. Cl.
CPC .............. *A61B 34/32* (2016.02); *A61B 50/13* (2016.02); *A61B 90/361* (2016.02); *A61B 90/37* (2016.02); *H02K 1/272* (2013.01)

(58) Field of Classification Search
CPC .............. A61B 17/1615; A61B 17/163; A61B 17/1633; A61B 17/162; A61B 17/1622; A61B 17/167; A61B 17/1679; A61B 34/00; A61B 34/30; A61B 34/32; A61B 34/37; A61B 34/70; A61B 34/71; A61B 34/77; A61B 19/00; A61B 90/00; A61B 90/36; A61B 90/361; A61B 90/37; B25J 9/00; B25J 9/041; B25J 9/16; B25J 9/164; B25J 9/1646; B25J 9/168; B25J 9/1689; B25J 15/00; B25J 15/02; G02B 21/00
See application file for complete search history.

(56) References Cited

U.S. PATENT DOCUMENTS

| | | | |
|---|---|---|---|
| 7,015,396 B2 | 3/2006 | Wada et al. | |
| 8,405,275 B2 | 3/2013 | Calley et al. | |
| 10,128,714 B2* | 11/2018 | Kokubo | H02K 3/34 |
| 2004/0051417 A1 | 3/2004 | Yamazaki et al. | |
| 2007/0138992 A1* | 6/2007 | Prisco | A61B 34/30 |
| | | | 318/568.21 |
| 2008/0058671 A1 | 3/2008 | Wiksell et al. | |
| 2010/0141079 A1 | 6/2010 | Chu et al. | |
| 2010/0204713 A1 | 8/2010 | Ruiz Morales | |
| 2011/0109189 A1 | 5/2011 | Taema | |
| 2011/0248507 A1 | 10/2011 | Petersen et al. | |
| 2012/0217827 A1 | 8/2012 | Takeuchi et al. | |
| 2013/0221781 A1* | 8/2013 | Nakayama | H02K 1/185 |
| | | | 310/89 |
| 2014/0028118 A1 | 1/2014 | Sakano | |

FOREIGN PATENT DOCUMENTS

| | | |
|---|---|---|
| CN | 103568015 A | 2/2014 |
| DE | 19843951 A1 | 12/1999 |
| EP | 1639947 A1 | 3/2006 |
| EP | 2153987 A1 | 2/2010 |
| JP | 55-107992 U | 7/1980 |
| JP | 55-107992 A | 8/1980 |
| JP | 56-3534 A | 1/1981 |
| JP | 56-003534 A | 1/1981 |
| JP | 08-308162 A | 11/1996 |
| JP | 2002-516141 A | 6/2002 |
| JP | 2002-281707 A | 9/2002 |
| JP | 2004-112975 A | 4/2004 |
| JP | 2008-514270 A | 5/2008 |
| JP | 2010-200775 A | 9/2010 |
| JP | 2011-135736 A | 7/2011 |
| JP | 4731562 B2 | 7/2011 |
| JP | 2012-005646 A | 1/2012 |
| JP | 2013-516301 A | 5/2013 |
| JP | 2013-236434 A | 11/2013 |
| JP | 2013-236436 A | 11/2013 |
| JP | 2014/187739 A | 10/2014 |
| JP | 2014-187739 A | 10/2014 |
| WO | 99/60944 A1 | 12/1999 |
| WO | 2006/036108 A1 | 4/2006 |
| WO | 2006/124390 A1 | 11/2006 |
| WO | 2006/124390 A2 | 11/2006 |
| WO | 2009/019562 A2 | 2/2009 |

OTHER PUBLICATIONS

Office Action for EP Patent Application No. 16751454.6, dated Sep. 18, 2018, 06 pages of Office Action.
Bakes, et al., Rigel 277 Plus, A Practical Guide to IEC 60601-1, Jun. 1, 2007, pp. 1-28.
Office Action for CN Patent Application No. 201680000769.0, dated Mar. 2, 2018, 05 pages of Office Action and 09 pages of English Translation.
Extended European Search Report of EP Patent Application No. 16751454.6, dated Oct. 27, 2017, 09 pages.
International Search Report and Written Opinion of PCT Application No. PCT/JP2016/052982, dated May 10, 2016, 06 pages of English Translation and 06 pages of ISRWO.
International Preliminary Report on Patentability of PCT Application No. PCT/JP2016/052982, dated Sep. 14, 2017, 07 pages of English Translation and 03 pages of IPRP.
Notice of Allowance and Fees Due for U.S. Appl. No. 15/121,466, dated Jun. 22, 2017, 07 pages.
Non-Final Rejection for U.S. Appl. No. 15/121,466, dated Feb. 12, 2017, 07 pages.
Non-Final Rejection for U.S. Appl. No. 15/121,466, dated Oct. 20, 2017, 05 pages.
Corrected Notice of Allowance in U.S. Appl. No. 15/121,466 dated Oct. 15, 2018.
Office Action for EP Patent Application No. 16751454.6, dated May 7, 2019, 08 pages of Office Action.
Office Action for JP Patent Application No. 2016-157181, dated May 28, 2019, 06 pages of Office Action and 05 pages of English Translation.
Office Action for JP Patent Application No. 2016-157181, dated Dec. 25, 2018, 07 pages of Office Action and 04 pages of English Translation.

* cited by examiner

MOTOR, ACTUATOR, AND MEDICAL SUPPORT ARM APPARATUS

CROSS-REFERENCE TO RELATED APPLICATIONS

The present application is a continuation application of U.S. patent application Ser. No. 15/121,466, filed Aug. 25, 2016, which is a National Stage Entry of PCT/JP2016/052982, filed Feb. 2, 2016, and claims the benefit of priority from prior Japanese Patent Application JP 2015-043761, filed Mar. 5, 2015, the entire content of which is hereby incorporated by reference.

TECHNICAL FIELD

The present disclosure relates to a motor, an actuator, and a medical support arm apparatus.

BACKGROUND ART

Recently, in the medical field, support arm apparatuses are being used to support surgeries and examinations. For example, a method is proposed in which an observation unit such as a camera for observing a surgical site is provided on the front edge of an arm unit of a support arm apparatus, and the surgeon performs surgery while viewing an image captured by the observation unit. Also proposed is a method of causing a support arm apparatus to perform work that has been done manually in the past, such as supporting a treatment tool such as forceps with the arm unit of a support arm apparatus.

At this point, generally, in medical electrical equipment (ME equipment), it is necessary to provide the insulation demanded by a certain safety standard (for example, the international safety standard IEC 060601-1) to protect the patient and the operator (surgeon). For example, in the case of a support arm apparatus having a movable mechanism in which an actuator is provided in a joint unit, there is demand to insulate the motor of the actuator so as to satisfy a certain safety standard.

For example, as a technology related to the insulation of a motor, Patent Literature 1 discloses a technology whereby the outer casing of the motor is made up of an insulating resin. According to this technology, by having the thickness of the insulating resin constituting the outer casing satisfy a required thickness determined by a safety standard, it becomes possible to ensure high reliability with regard to safety factors such as shock prevention.

CITATION LIST

Patent Literature

Patent Literature 1: JP H8-308162A

SUMMARY OF INVENTION

Technical Problem

However, in the case of applying a method of constructing the outer casing of the motor with an insulating resin of a certain thickness, like the technology described in Patent Literature 1, to a support arm apparatus, there is a possibility of the motor becoming bulkier, or in other words, the actuator may become bulkier, and as a result, the arm unit may be bulkier.

On the other hand, if usage in the medical field is considered, there is demand for the arm unit of the support arm apparatus to be more compact. This is because if the configuration of the arm unit is large, there is a risk that the workspace of the surgeon performing surgery and the surgeon's field of view may be limited by the arm unit, thereby inhibiting smooth work.

In this way, in a movable mechanism of medical electrical equipment such as the joint unit of a medical support arm apparatus, there is demand for a technology that achieves a more compact configuration and also ensures high safety by satisfying a certain safety standard. Accordingly, the present disclosure proposes a new and improved motor, actuator, and medical support arm apparatus capable of being configured more compactly and also capable of ensuring higher safety.

Solution to Problem

According to the present disclosure, there is provided a motor. An electrically active part is provided with an insulating structure so that insulating properties between the electrically active part and one or more conductors near the electrically active part satisfy a certain safety standard regarding medical electrical equipment.

According to the present disclosure, there is provided an actuator, including: a motor in which an electrically active part is provided with an insulating structure so that insulating properties between the electrically active part and one or more conductors near the electrically active part satisfy a certain safety standard regarding medical electrical equipment. The actuator is used in a drive mechanism of medical electrical equipment.

According to the present disclosure, there is provided a medical support arm apparatus, including: an arm unit made up of a plurality of joint units; and a medical tool provided on a front edge of the arm unit. In a motor of an actuator provided in the joint unit, an electrically active part is provided with an insulating structure so that insulating properties between the electrically active part and one or more conductors near the electrically active part satisfy a certain safety standard regarding medical electrical equipment.

According to the present disclosure, an electrically active part inside a motor is provided with an insulating structure so that the insulating properties between the electrically active part and one or more conductors near the electrically active part satisfy a certain safety standard regarding medical electrical equipment. Consequently, when such a motor is built into a movable mechanism, it is not necessary to provide an insulating structure between the motor and another member to which the motor is attached. Consequently, it becomes possible to realize a movable mechanism capable of being configured more compactly and also capable of ensuring higher safety.

Advantageous Effects of Invention

According to the present disclosure as described above, it becomes possible to realize a movable mechanism capable of being configured more compactly and also capable of ensuring higher safety. Note that the effects described above are not necessarily limited, and along with or instead of the effects, any effect that is desired to be introduced in the present specification or other effects that can be expected from the present specification may be exhibited.

DESCRIPTION OF EMBODIMENT(S)

Figure 1:
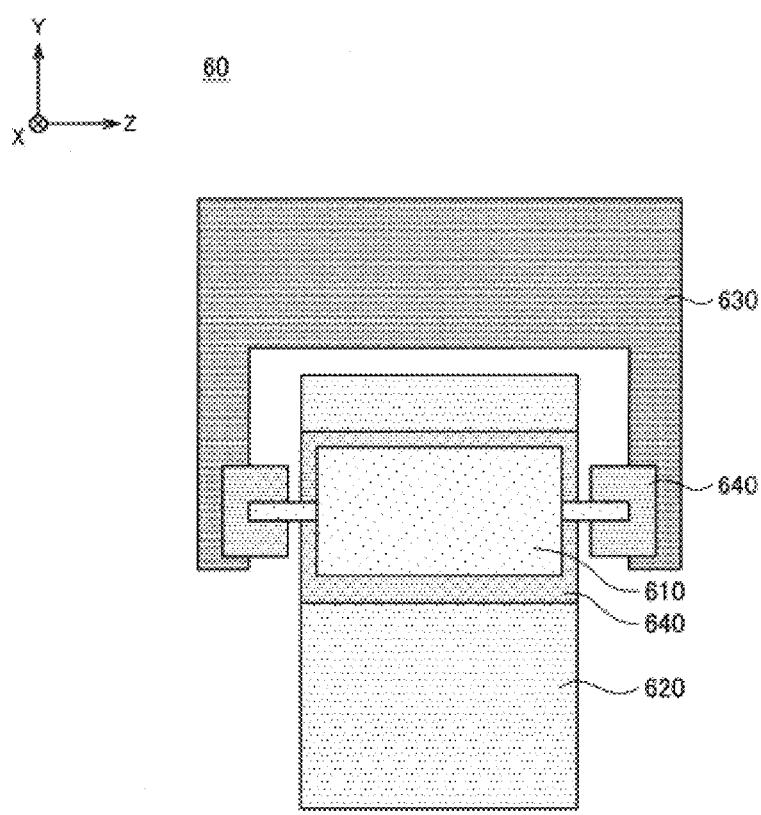
FIG. 1 is a schematic diagram illustrating an example of a typical insulated movable mechanism.

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

Hereinafter, the description will proceed in the following order.
1. Typical methods of insulating movable mechanism
   1-1. Method of covering motor with insulator
   1-2. Method of covering movable mechanism with insulator
   1-3. Investigation into typical insulation methods
2. First Embodiment
3. Second Embodiment
4. Summary of first and second embodiments
5. Application example
   5-1. Overview of support arm apparatus
   5-2. Overall configuration of support arm apparatus
   5-3. Configuration of actuator
6. Supplement Herein, the present disclosure relates to the insulation of medical electrical equipment including a movable mechanism rotationally driven by an actuator. As discussed above, in medical electrical equipment, it is necessary to provide the insulation demanded by a certain safety standard. In the following description, the case in which the safety standard is IEC 060601-1 (corresponding to JIS T 0601-1 in JIS), which is used widely as an international safety standard for medical electrical equipment, will be described as an example. However, the present disclosure is not limited to such an example, and the safety standard applied to the medical electrical equipment may be another standard.

According to IEC 060601-1, for example, certain insulating properties must be ensured between an electrically active part, such as the coil of a motor inside the medical electrical equipment, and a member of the medical electrical equipment that may be touched by people (such as the operator or the patient). Herein, in this specification, the "electrically active part" means a conductive portion intended to carry current during normal usage. In the case of a motor, components such as a coil, a harness for leading current to the coil from an external source, and a substrate that receives current from an external power source to which the harness may be connected correspond to the electrically active part.

In a typical motor, the coil may be made up of enameled wire coated with an insulating sheath, but the insulating properties of enameled wire sheaths often do not satisfy the demands of IEC 060601-1. Consequently, in a typical motor, the motor itself is considered to be insufficiently insulated. Thus, in medical electrical equipment using a typical motor, the motor is provided with an insulating structure that satisfies the insulating properties stipulated by IEC 060601-1. Note that according to IEC 060601-1, the insulating structure may be realized by providing an insulator (solid insulation) having certain insulation performance, or by providing a certain clearance distance and a certain creepage distance, between the electrically active part and nearby conductors.

In the following, first, typical existing methods of insulating the movable mechanism of medical electrical equipment will be described in (1. Typical methods of insulating movable mechanism). Next, preferred embodiments of the present disclosure conceived by the inventors will be described in (2. First embodiment) and (3. Second embodiment). Next, the advantageous effects and the like exhibited by the first and second embodiments described thus far will be summarized in (4. Summary of first and second embodiments). Furthermore, as an application example of a motor according to the first and second embodiments of the present disclosure, the configuration of a support arm apparatus including an actuator to which such a motor is applied will be described in (5. Application example).

1. Typical Methods of Insulating Movable Mechanism

At this point, before describing preferred embodiments of the present disclosure, to further clarify the present disclosure, the results of an investigation by the inventors into typical existing methods of insulating a movable mechanism of medical electrical equipment will be described, and in addition, the background behind the inventors' conception of the present disclosure will be described.

(1-1. Method of Covering Motor with Insulator)

An example of a typical method of insulating a movable mechanism will be described with reference to FIG. 1. FIG. 1 is a schematic diagram illustrating an example of a typical insulated movable mechanism.

In FIG. 1, a movable mechanism of medical electrical equipment is illustrated schematically. Referring to FIG. 1, a movable mechanism 60 is made up of a stationary part 620, a motor 610 connected to the stationary part 620, and a movable part 630 which is connected to a drive shaft of the motor 610 and which drives rotationally with respect to the stationary part 620 due to the driving of the motor 610. In the movable mechanism 60, the stationary part 620 and the movable part 630 correspond to parts that may be touched by the patient and the operator, and include an outer covering made of a metal chassis, for example. Note that in FIG. 1, as well as in FIGS. 2 and 3 discussed later, in order to make the relationships among the arrangement of the respective members easier to understand, the respective members are shaded with different types of hatching for the sake of convenience.

Note that in the following description, when the configuration of the movable mechanism and the motor are being described, the direction of the drive shaft of the motor (that is, the rotary axis direction) is also called the Z axis direction. Also, the two mutually orthogonal directions in the plane perpendicular to the Z axis direction are also called the X axis direction and the Y axis direction, respectively.

As illustrated in the drawing, in the movable mechanism 60, solid insulation 640 (an insulator 640) is provided between the housing of the motor 610 and the stationary part 620, and also between the drive shaft of the motor 610 and the movable part 630. The insulator 640 is formed from an insulating resin or the like, for example, and the material, thickness, and the like are adjusted so as to satisfy the insulating properties stipulated by IEC 060601-1. Consequently, the insulating properties between the motor 610 and the stationary part 620, and also between the motor 610 and the movable part 630, satisfy the demands of IEC 060601-1, and the safety of the patient and the operator contacting the stationary part 620 and the movable part 630 is maintained. In this way, a method of covering the motor 610 with an insulator is given as one example of a typical method of insulating a movable mechanism. The technology described in Patent Literature 1 above may be considered to conform to this method.

(1-2. Method of Covering Movable Mechanism with Insulator)

Figure 2:
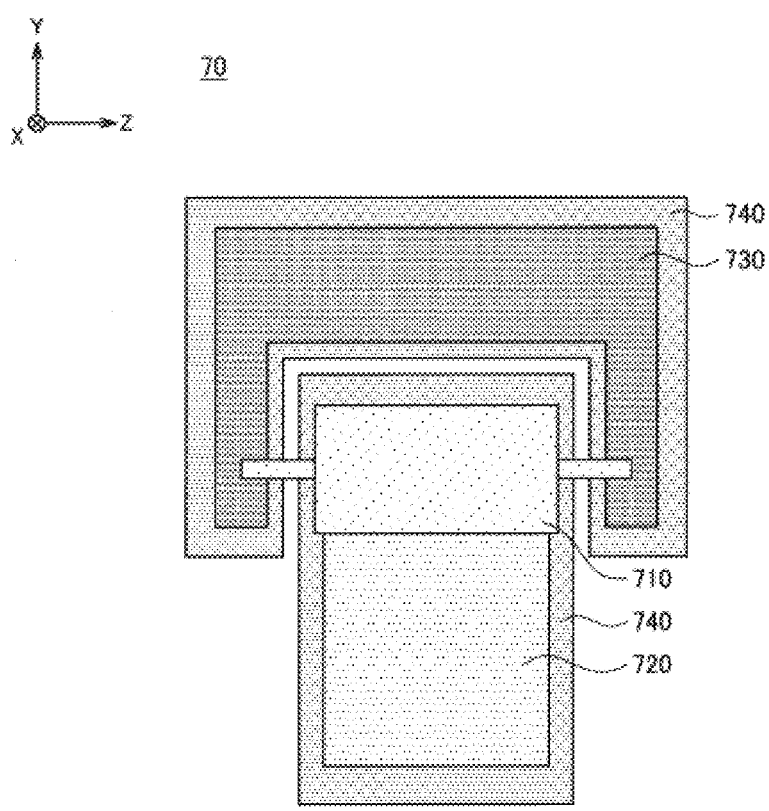
FIG. 2 is a schematic diagram illustrating another example of a typical insulated movable mechanism.

Another example of a typical method of insulating a movable mechanism will be described with reference to FIG. 2. FIG. 2 is a schematic diagram illustrating another example of a typical insulated movable mechanism.

In FIG. 2, similarly to FIG. 1, a movable mechanism of medical electrical equipment is illustrated schematically. Referring to FIG. 2, a movable mechanism 70 is made up of a stationary part 720, a motor 710 connected to the stationary part 720, and a movable part 730 which is connected to a drive shaft of the motor 710 and which drives rotationally with respect to the stationary part 720 due to the driving of the motor 710. In the movable mechanism 70, the stationary part 720 and the movable part 730 correspond to parts that may be touched by the patient and the operator, and include an outer covering made of a metal chassis, for example.

As illustrated in the drawing, in the movable mechanism 70, solid insulation 740 (an insulator 740) is provided so as to cover the entire movable mechanism 70. The insulator 740 is formed from an insulating resin or the like, for example, and the material, thickness, and the like are adjusted so as to satisfy the insulating properties stipulated by IEC 060601-1. Consequently, the patient and the operator contact the stationary part 720 and the movable part 730 through the insulator 740 which ensures certain insulating properties, and thus the safety of the patient and the operator is maintained. In this way, a method of covering the movable mechanism 70 with an insulator is given as another example of a typical method of insulating a movable mechanism.

(1-3. Investigation into Typical Insulation Methods)

Herein, recently, in the medical field, support arm apparatuses are being used to support surgeries and examinations. In a support arm apparatus including a drive shaft, by providing an actuator in a joint unit corresponding to the drive shaft, and controlling the driving of the motor of the actuator, the position and the orientation of the arm unit is controlled. In this way, the joint unit of a medical support arm apparatus corresponds to the movable mechanisms 60 and 70 discussed above, and insulating properties conforming to IEC 060601-1 are demanded of the joint unit.

On the other hand, in a medical support arm apparatus, there is demand for the arm unit to be more compact. This is because if the configuration of the arm unit is large, there is a risk that the workspace of the surgeon performing surgery and the surgeon's field of view may be limited by the arm unit, thereby inhibiting smooth work. Also, since many medical staff members and other medical equipment exist in the operating room, a more compact medical support arm apparatus is demanded so as not to interfere with these nearby people and objects.

Given the above circumstances, consider the case of applying the typical insulating methods described above to the joint unit of a medical support arm apparatus. First, in the case of applying the method of covering the motor 610 with an insulator, the motor 610 becomes bulkier, and thus the actuator becomes bulkier, and as a result, there are concerns that the arm unit may become bulkier. Also, with this method, since the insulator 640 is also provided on the drive shaft of the motor 610, there is a possibility that the output torque of the motor 610 may be limited so that the insulator 640 does not become deformed or ruptured. Attempting to ensure the output torque of the motor 610 requires a bulkier insulator 640 to improve the strength of the insulator 640, and the arm unit becomes even bulkier.

Meanwhile, in the case of applying the method of covering the entire movable mechanism 70 with an insulator, the entire arm unit becomes covered with an insulator, and thus there are obvious concerns that the arm unit may become bulkier. In addition, since the insulator 740 must be disposed so as not to inhibit the operation of the arm unit and also so that the arm unit does become exposed even when operated, the number of component parts increases, and the design difficulty also increases. Increased complexity in the configuration also leads to concerns that assembly work and maintenance work may become complicated. Furthermore, by covering the entire arm unit with an insulator, the heat produced by the motor and the like is less readily dissipated externally, and there is also a risk that normal operation of the medical electrical equipment may be inhibited.

In this way, with typical existing technologies, in an actuator provided in a movable mechanism of medical electrical equipment such as the joint unit of a medical support arm apparatus, it is difficult to achieve a more compact configuration and also ensure high safety by satisfying a certain safety standard. Accordingly, in light of these circumstances, the inventors investigated technologies capable of achieving a more compact configuration while also ensuring high safety by satisfying a certain safety standard in an actuator, and as a result, conceived the preferred embodiments of the present disclosure indicated below. The following describes in detail preferred embodiments of the present disclosure conceived by the inventors.

2. First Embodiment

Figure 3:
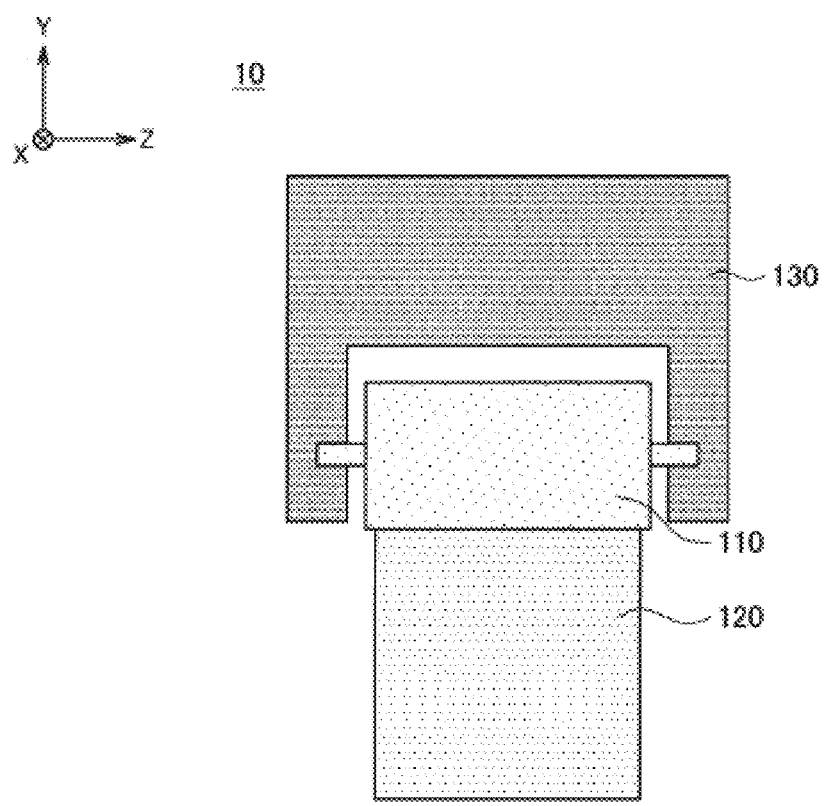
FIG. 3 is a schematic diagram illustrating an example configuration of a movable mechanism of medical electrical equipment to which a motor according to a first embodiment has been applied.
Figure 4:
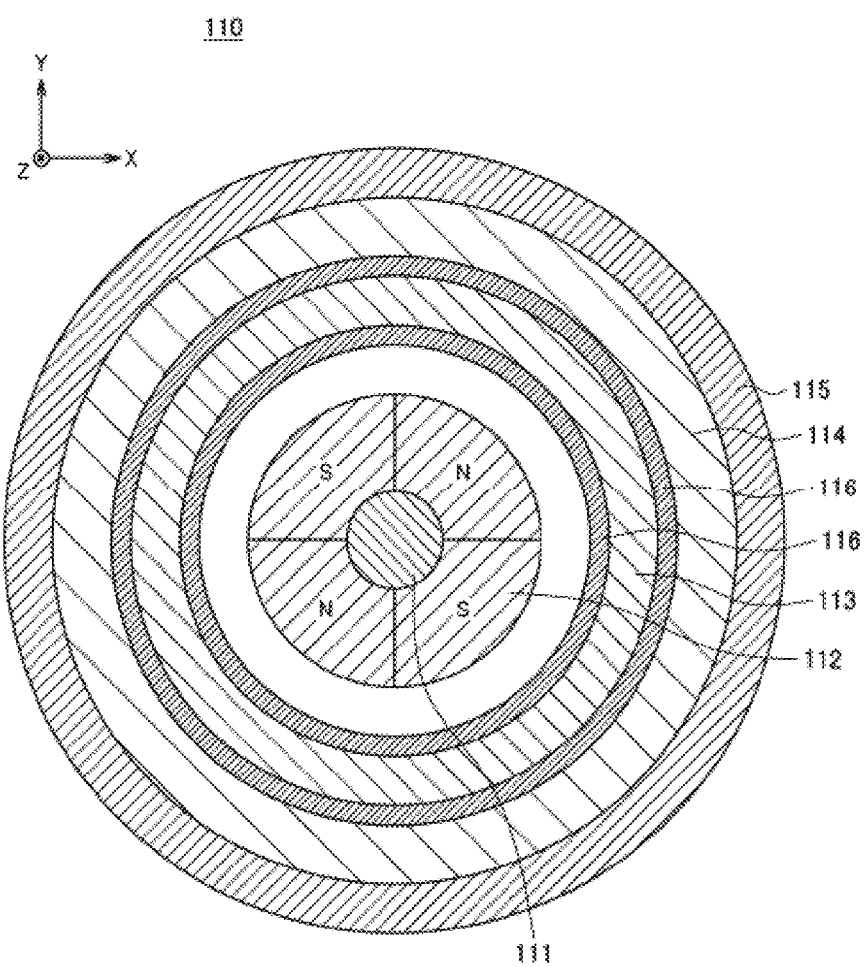
FIG. 4 is a cross-sectional view of a plane (X-Y plane) perpendicular to a drive shaft of a motor according to a first embodiment.
Figure 5:
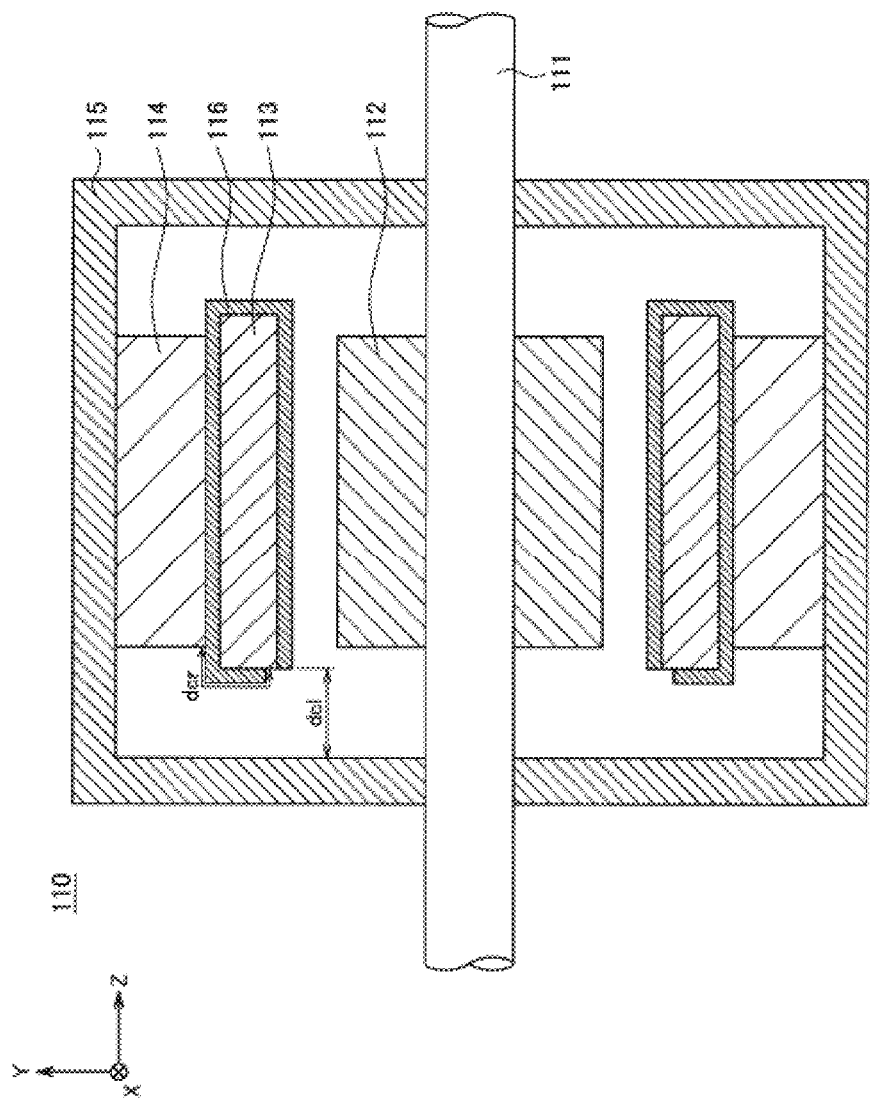
FIG. 5 is a cross-sectional view of a plane (Y-Z plane) passing through and parallel to a drive shaft of a motor according to a first embodiment.

A configuration of a motor according to the first embodiment of the present disclosure will be described with reference to FIGS. 3 to 5. FIG. 3 is a schematic diagram illustrating an example configuration of a movable mechanism of medical electrical equipment to which a motor according to a first embodiment has been applied. FIG. 4 is a cross-sectional view of a plane (X-Y plane) perpendicular to a drive shaft of a motor according to a first embodiment. FIG. 5 is a cross-sectional view of a plane (Y-Z plane) passing through and parallel to a drive shaft of a motor according to a first embodiment.

In FIG. 3, a movable mechanism of medical electrical equipment to which a motor according to a first embodiment has been applied is illustrated schematically. Referring to FIG. 3, a movable mechanism 10 is made up of a stationary part 120, a motor 110 connected to the stationary part 120, and a movable part 130 which is connected to a drive shaft of the motor 110 and which drives rotationally with respect to the stationary part 120 due to the driving of the motor 110. In the movable mechanism 10, the stationary part 120 and the movable part 130 correspond to parts that may be touched by the patient and the operator. For example, the movable mechanism 10 corresponds to a joint unit constituting an arm unit of a medical support arm apparatus. Also, for example, the stationary part 120 and the movable part 130 are parts corresponding to links constituting the arm unit of the medical support arm apparatus, and including an outer covering made of a metal chassis, for example.

As discussed later with reference to FIGS. 4 and 5, in the first embodiment, inside the motor 110, an electrically active part such as a coil 113 is provided with an insulating structure in which the insulating properties between the electrically active part and one or more conductors near the electrically active part satisfy a certain safety standard (for example, IEC 060601-1). Note that conducting members existing near the electrically active part include various types of conductive components from among the components constituting the motor, such as an iron core, a motor outer covering (housing), bearings, a rotor shaft (drive shaft), and a magnet. Consequently, in the first embodiment, as illustrated in FIG. 3, it is not necessary to provide an insulator between the motor 110 and the stationary part 120 and also between the motor 110 and the movable part 130, or to provide an insulator so as to cover the stationary part 120 and the movable part 130. Thus, according to the first embodiment, it becomes possible to make the movable mechanism 10 more compact compared to the typical methods discussed earlier.

A configuration of the motor 110 according to the first embodiment will be described in further detail with reference to FIGS. 4 and 5. Referring to FIGS. 4 and 5, the motor 110 is equipped with a drive shaft 111, an approximately cylindrical housing 115 that rotatably supports the drive shaft 111 through bearings (not illustrated), a magnet 112, which is provided so as to cover, in the circumferential direction, part of the outer circumference of the drive shaft 111 in the rotary shaft direction, and which rotates together with the drive shaft 111, an approximately cylindrical coil 113 provided inside the housing 115 so as to face the magnet 112, and an approximately cylindrical back yoke 114 provided on the inner wall of the housing 115 so as to face the magnet 112 through the coil 113. Additionally, in the motor 110, solid insulation 116 (an insulator 116) is provide so as to cover the perimeter of the coil 113.

By applying a current to the coil 113 and also switching the direction of the current at appropriate timings, the interaction between the magnetic field produced by the coil 113 and the magnetic field from the magnet 112 cause the drive shaft 111 to rotate. In addition, the back yoke 114 is a member provided to minimize magnetic flux leakage and raise the magnetic flux density linking the coil 113, and is formed by layering multiple thin plates made of soft magnetic material, such as an iron alloy with added Si, for example.

In this way, the motor 110 corresponds to a typical brushless motor that is referred to as coreless, in which the insulator 116 is provided between the coil 113 and nearby conductors (such as the back yoke 114 and the housing 115, for example). Note that for the drive shaft 111, the magnet 112, the coil 113, the back yoke 114, and the housing 115, various configurations used in typical coreless brushless motors may be applied, and thus a detailed description of these members will be reduced or omitted. Herein, in the motor 110, in order to satisfy the insulating properties stipulated by IEC 060601-1, it is necessary to provide the electrically active part, that is, the coil 113, with an insulating structure that satisfies the insulating properties stipulated by IEC 060601-1. According to IEC 060601-1, the insulating structure may be realized by providing an insulator (solid insulation) having certain insulation performance, or by providing a certain clearance distance and a certain creepage distance, between the electrically active part and nearby conductors. At this point, the insulating properties demanded of the insulator, as well as the distances demanded of the clearance distance and the creepage distance, may be decided based on IEC 060601-1 according to factors such as the power source voltage and the usage environment of the motor 110, for example.

In the first embodiment, the insulator 116 is provided so as to cover the perimeter of the coil 113, as discussed above. Additionally, the material and the thickness of the insulator 116 are adjusted so as to satisfy the insulating properties stipulated by IEC 060601-1. Note that the insulator 116 may be a sheet-like member made of a resinous material, for example. However, the first embodiment is not limited to such an example, and any of various types of known materials and shapes may be used as the insulator 116, insofar as the desired insulating properties may be realized.

On the other hand, in the illustrated example, on part of the coil 113, there exists an opening not covered by the insulator 116. This opening may be the part where a harness or the like for leading current from an external source to the coil 113 is connected to the coil 113, for example. In the first embodiment, factors such as the positional relationship between the coil 113 and the housing 115, the positional relationship between the coil 113 and the back yoke 114, and/or the formation position of the insulator 116 (that is, the formation position of the opening on the insulator 116) are adjusted so that enough distance as stipulated by IEC 060601-1 is ensured as the clearance distance and the creepage distance between the coil 113 and the nearby conductors through the opening. In FIG. 5, a simulated clearance distance dcl between the coil 113 and the housing 115 and a simulated creepage distance dcr between the coil 113 and the back yoke 114 are illustrated as an example. Note that when a harness is connected to the coil 113 as above, the harness may also be an electrically active part, and thus the harness may also be subjected to treatment, such as being covered by the insulator 116, or by providing a certain clearance distance and a certain creepage distance around the harness, for example.

In the motor 110 according to the first embodiment, as described above, the insulator 116 satisfying the stipulations of IEC 060601-1, as well as a certain clearance distance and a certain creepage distance satisfying the stipulations of IEC 060601-1, are provided between the electrically active part, namely the coil 113, and nearby conductors. Consequently, since the insulating properties stipulated by IEC 060601-1 are ensured for the members exposed to the outside of the motor 110, such as the drive shaft 111 and the housing 115, it is not necessary to provide an additional insulator between the motor 110 and nearby members, as illustrated in FIG. 3. Thus, according to the first embodiment, it becomes possible to make the movable mechanism 10 more compact, while still satisfying the stipulations of IEC 060601-1.

Note that in the example illustrated in FIG. 5, to insulate the coil 113, the perimeter of the coil 113 is covered by the insulator 116, while in addition, a certain clearance distance and a certain creepage distance are ensured at an opening not covered by the insulator 116. However, the first embodiment is not limited to such an example. As discussed above, according to the IEC 060601-1, it is sufficient to ensure insulating properties by providing an insulator having certain insulation performance between the electrically active part, namely the coil 113, and nearby conductors, or by providing a certain clearance distance and a certain creepage distance. The method of realizing an insulating structure for insulating the coil 113 is not limited to the example illustrated in the drawings.

For example, if it is possible to provide a certain clearance distance and a certain creepage distance between the coil 113 and nearby conductors over the entire perimeter of the coil 113, the insulator 116 does not need to be provided. Alternatively, if it is possible to cover with the insulator 116 the entire perimeter of electrically active parts, such as the coil 113 and the harness discussed above, for example, the certain clearance distance and the certain creepage distance do not need to be provided on the perimeters of these electrically active parts. The way in which to realize an insulating structure may be configured appropriately according to factors such as the structure of the motor 110.

Generally, however, in a motor, it is known that if the distance between the coil and the magnet is long, the interaction of the magnetic fields between the two will weaken, and the output torque of the motor will decrease. By providing an insulating structure, the distance between the coil 113 and the magnet 112 may also vary, and thus when providing the motor 110 with an insulating structure, preferably the specific configuration of the insulating structure is decided while also accounting for the performance demanded on the motor 110 according to the application.

Also, in the example illustrated in FIGS. 4 and 5, the case of insulating the coil 113 as an example of the electrically active part is illustrated, but the first embodiment is not limited to such an example. Inside the motor 110, other components that may function as an electrically active part may exist besides the coil 113, such as the harness discussed earlier, and a substrate that receives current from an external power source to which the harness may be connected. In the first embodiment, if other electrically active parts besides the coil 113 exist, these other electrically active parts may also be provided with an insulating structure conforming to IEC 060601-1, similarly to the coil 113.

The above thus describes a configuration of the motor 110 according to the first embodiment with reference to FIGS. 3 to 5. Note that the configuration of the motor 110 is not limited to the example illustrated in FIGS. 4 and 5, and the motor 110 may also be configured so that the insulator 116 is provided for any of various known types of coreless brushless motors.

3. Second Embodiment

Figure 6:
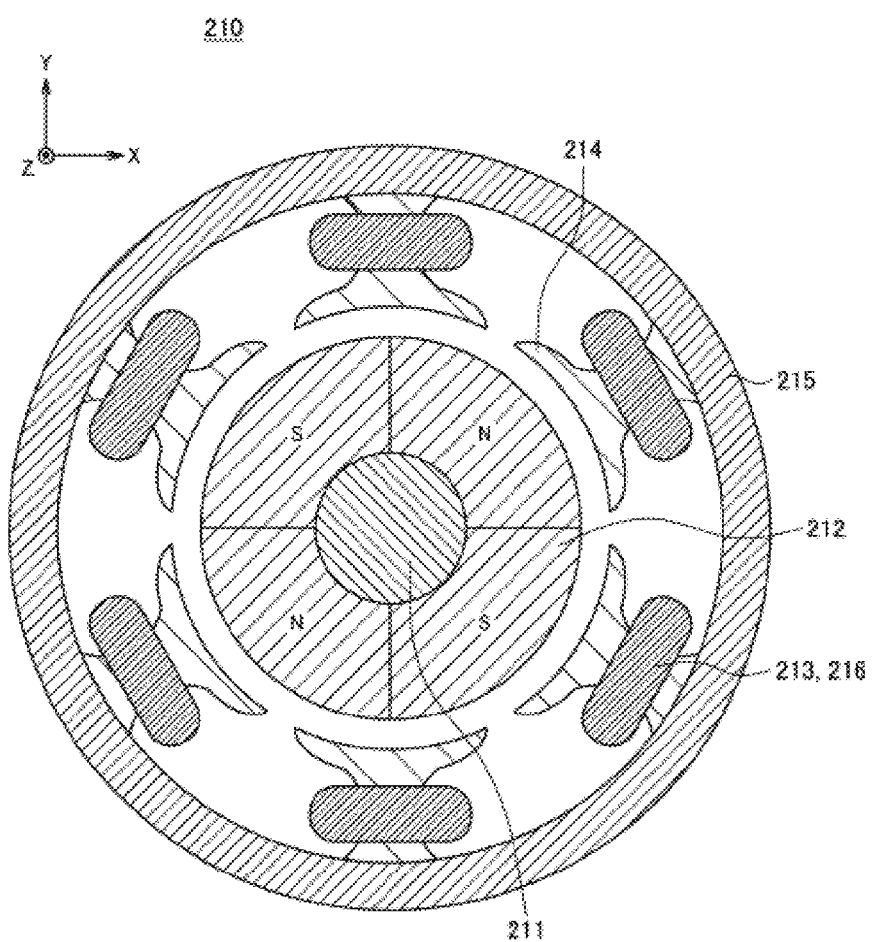
FIG. 6 is a cross-sectional view of a plane (X-Y plane) perpendicular to a drive shaft of a motor according to a second embodiment.
Figure 7:
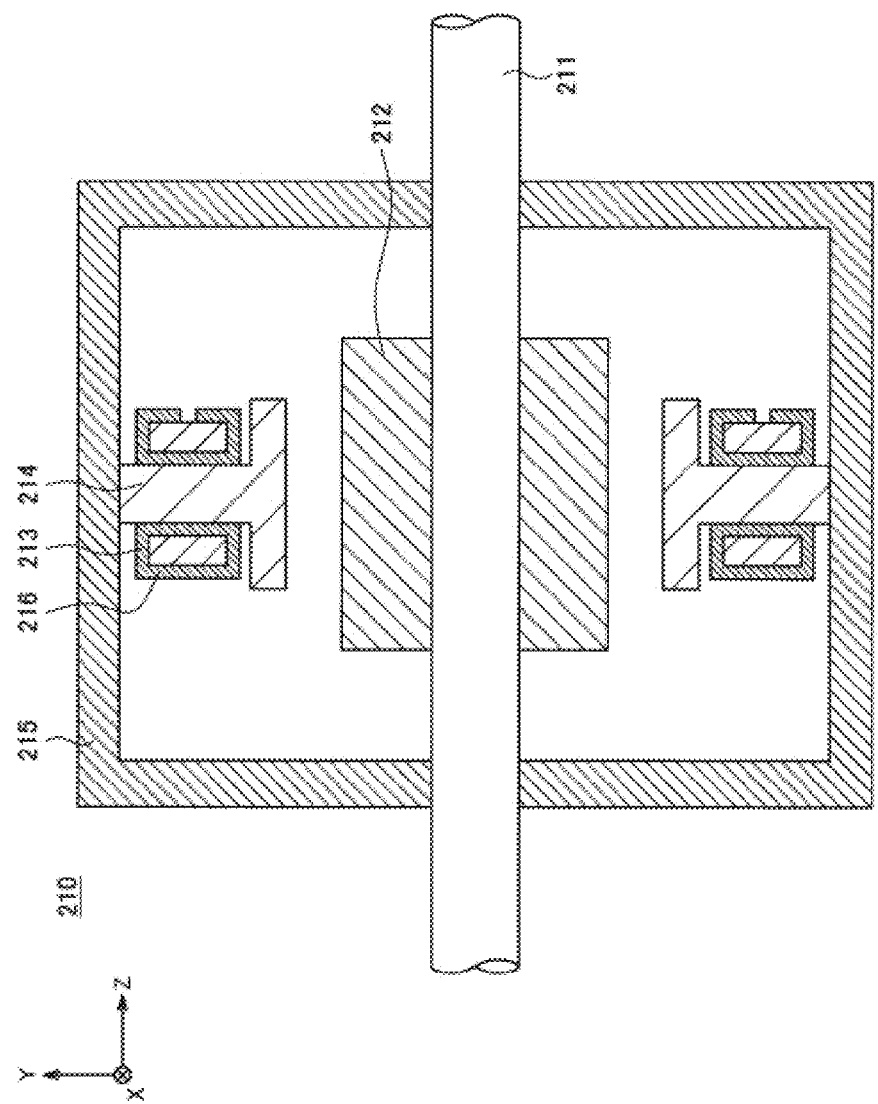
FIG. 7 is a cross-sectional view of a plane (Y-Z plane) passing through and parallel to a drive shaft of a motor according to a second embodiment.

A configuration of a motor according to the second embodiment of the present disclosure will be described with reference to FIGS. 6 and 7. FIG. 6 is a cross-sectional view of a plane (X-Y plane) perpendicular to a drive shaft of a motor according to the second embodiment. FIG. 7 is a cross-sectional view of a plane (Y-Z plane) passing through and parallel to a drive shaft of a motor according to the second embodiment. Note that the configuration of the movable mechanism that may be installed onboard the motor according to the second embodiment is similar to the movable mechanism 10 according to the first embodiment illustrated in FIG. 3. Consequently, in the following description of the second embodiment, the configuration of the motor according to the second embodiment will be described primarily, whereas description of the movable mechanism that may be installed onboard the motor will be reduced or omitted.

Referring to FIGS. 6 and 7, the motor 210 according to the second embodiment is equipped with a drive shaft 211, an approximately cylindrical housing 215 that rotatably supports the drive shaft 211 through bearings (not illustrated), a magnet 212, which is provided so as to cover, in the circumferential direction, part of the outer circumference of the drive shaft 211 in the rotary shaft direction, and which rotates together with the drive shaft 211, multiple stator cores 214 projecting inward from the inner wall of the housing 215, and coils 213 which are configured by winding conductive wire around the perimeter of each stator core 214 and which are provided so as to face the magnet 212. Additionally, in the motor 210, an insulator 216 (insulator 216) is provided so as to cover the perimeter of the coil 213 provided on each stator core 214.

By applying a current to the coils 213 and also switching the direction of the current at appropriate timings, the interaction between the magnetic field produced by the coils 213 and the magnetic field from the magnet 212 cause the drive shaft 211 to rotate. In this way, the motor 210 corresponds to a typical brushless motor having stator cores 214, in which the insulators 216 are provided between the coils 213 and nearby conductors (such as the stator cores 214 and the housing 215, for example). Note that for the drive shaft 211, the magnet 212, the coils 213, the stator cores 214, and the housing 215, various configurations used in typical brushless motors having stator cores may be applied, and thus a detailed description of these members will be reduced or omitted.

Similarly to the first embodiment, the material and the thickness of the insulators 216 covering the coils 213 are adjusted so as to satisfy the insulating properties stipulated by IEC 060601-1. The insulators 216 may be made of a resinous material, for example. However, the second embodiment is not limited to such an example, and any of various types of known materials and shapes may be used as the insulators 216, insofar as the desired insulating properties may be realized.

In addition, as illustrated in FIG. 7, likewise in the second embodiment, an opening which is for connecting a harness or the like to the coils 213 and which is not covered by the insulators 216 may also exist in part of the coils 213. In this way, if an opening not covered by the insulators 216 exists in part of the coils 213, factors such as the positional relationship between the coils 213 and the housing 215, the positional relationship between the coils 213 and the stator cores 214, and/or the formation position of the insulators 216 (that is, the formation position of the opening on the insulators 116) may be adjusted so that enough distance as stipulated by IEC 060601-1 is ensured as the clearance distance and the creepage distance between the coils 213 and the nearby conductors through the opening (for the sake of simplicity, in FIG. 7, illustration of the clearance distance dcl and the creepage distance dcr is omitted). Note that, similarly to the first embodiment, when harnesses are connected to the coils 213 as above, the harnesses may also be subjected to treatment, such as being covered by the insulators 216, or by providing a certain clearance distance and a certain creepage distance around the harnesses, for example.

As described above, in the motor 210 according to the second embodiment, similarly to the motor 110 according to the first embodiment, the insulators 216 satisfying the stipulations of IEC 060601-1, as well as a certain clearance distance and a certain creepage distance satisfying the stipulations of IEC 060601-1, likewise are provided between the electrically active part, namely the coils 213, and nearby conductors. Consequently, since the insulating properties stipulated by IEC 060601-1 are ensured for the members exposed to the outside of the motor 210, such as the drive shaft 211 and the housing 215, it is not necessary to provide an additional insulator between the motor 210 and nearby members in the case of applying the motor 210 to the movable mechanism 10 as illustrated in FIG. 3. Thus, likewise in the second embodiment, it becomes possible to make the movable mechanism 10 more compact, while still satisfying the stipulations of IEC 060601-1.

Note that, similarly to the first embodiment, in the second embodiment, it is likewise sufficient to ensure insulating properties by providing insulators having certain insulation performance between the electrically active part, namely the coils 213, and nearby conductors, or by providing a certain clearance distance and a certain creepage distance. The method of realizing an insulating structure for insulating the coils 213 is not limited to the example illustrated in the drawings. When providing the motor 210 with an insulating structure, preferably the insulating structure is decided while also accounting for changes in the performance of the motor 210 due to providing the insulating structure. Furthermore, in the example illustrated in FIGS. 6 and 7, the case of insulating the coils 113 as an example of the electrically active part is illustrated, but if other electrically active parts besides the coils 213 exist, these other electrically active parts may also be provided with an insulating structure conforming to IEC 060601-1, similarly to the coils 213.

The above thus describes a configuration of the motor 210 according to the second embodiment with reference to FIGS. 6 and 7. Note that the configuration of the motor 210 is not limited to the example illustrated in FIGS. 6 and 7, and the motor 210 may also be configured so that the insulator 216 is provided for any of various known types of brushless motors having stator cores.

4. Summary of First and Second Embodiments

As described above, in the motors 110 and 210 according to the first and second embodiments, inside the motors 110 and 210, the electrically active part is provided with an insulating structure in which the insulating properties between the electrically active part and nearby conductors satisfies a certain safety standard. Consequently, on the outside of the motors 110 and 210, it is not necessary to provide an insulating structure between the motors 110 and 210 and other members that contact the motors 110 and 210, and the motors 110 and 210 may be attached to such members directly. For this reason, it becomes possible to make the overall configuration of the movable mechanism 10 provided with the motor 110 or 210 more compact, while still ensuring the insulating properties stipulated by the certain safety standard.

Additionally, since the motors 110 and 210 may be attached directly to the metal chassis of the outer covering of other members (for example, the stationary part 120 and the movable part 130 illustrated in FIG. 3), heat produced by the motors 110 and 210 may be dissipated by the metal chassis, thereby making it possible to minimize rises in the temperature of the medical electrical equipment overall.

Herein, as described in (1. Typical methods of insulating movable mechanism) above, in the method of covering the motor 610 with an insulator, the drive shaft of the motor 610 is connected to the movable part 630 through the insulator 640, and thus there is a possibility that the output torque of the motor 610 may be limited so that the insulator 640 does not become deformed or ruptured. On the other hand, according to the first and second embodiments, as above, the drive shaft of the motors 110 and 210 may be attached directly to the movable part 130. Consequently, since the motor housing and the metal chassis of the movable part 130 may be used as strengthening components, the output torque of the motor 110 is not limited excessively compared to the case of the interposed insulator 640.

Additionally, as also described in (1. Typical methods of insulating movable mechanism) above, in the method of covering the entire movable mechanism 70 with an insulator, since the insulator 740 must be disposed so as not to inhibit the operation of the arm unit and also so that the arm unit does become exposed even when operated, there is a risk that the number of component parts may increase, and the design difficulty may also increase. On the other hand, according to the first and second embodiments, as above, the drive shaft of the motors 110 and 210 may be attached directly to the movable part 130, and thus the configuration may be simplified, and more lightweight and lower-cost medical electrical equipment may be realized.

Note that in the first and second embodiments described above, the case in which the motors 110 and 210 are brushless motors is described, but the present disclosure is not limited to such an example. The type of motor to which the insulating structure according to the first and second embodiments may be applied is not particularly limited, and the insulating structure may be applied to various known types of motors.

5. Application Example

As described above, the motors 110 and 210 according to the first and second embodiments have insulating properties that satisfy the IEC 060601-1 standard for medical electrical equipment. At this point, as one example of the application of the motors 110 and 210 to medical electrical equipment, a case in which the motors 110 and 210 are used in an actuator provided in a joint unit of a medical support arm apparatus used for medical procedures such as surgeries and examinations will be described. However, the medical electrical equipment to which the motors 110 and 210 may be applied is not limited to such an example, and the motors 110 and 210 may be applied to various types of medical electrical equipment having a drive mechanism.

(5-1. Overview of Support Arm Apparatus)

Before describing in detail the configuration of a support arm apparatus to which the motors 110 and 210 according to the first and second embodiments may be applied, a state of surgery using such a support arm apparatus will be described, and in addition, the features demanded of a medical support arm apparatus will be described.

Figure 8:
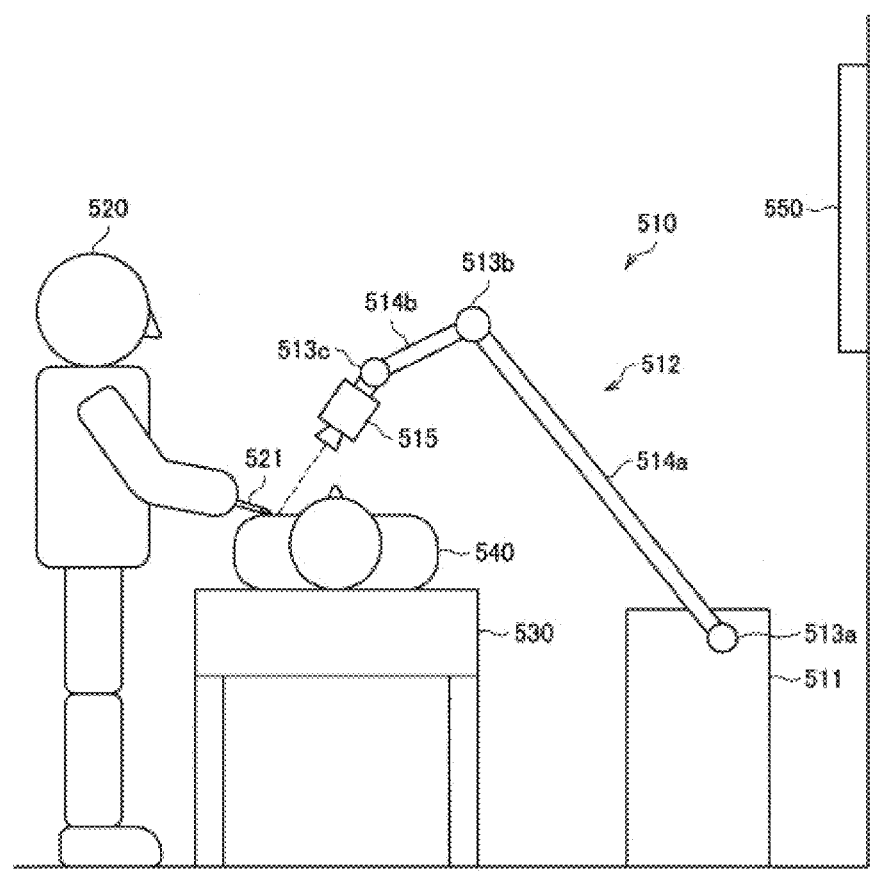
FIG. 8 is a schematic diagram illustrating a state of surgery using a support arm apparatus.

A state of surgery using a support arm apparatus will be described with reference to FIG. 8. FIG. 8 is a schematic diagram illustrating a state of surgery using a support arm apparatus.

FIG. 1 illustrates a state in which a surgeon 520 is using a surgical treatment tool 521, such as a scalpel, tweezers, or forceps, to perform surgery on a patient 540 lying on an operating table 530. Beside the operating table 530, a support arm apparatus 510 to which the motors 110 and 210 according to the first and second embodiments may be applied is provided.

The support arm apparatus 510 is equipped with a base unit 511 which acts as a base, and an arm unit 512 which extends from the base unit 511. Also, although omitted from illustration, the support arm apparatus 510 is equipped with a control device that controls the operation of the support arm apparatus 510 (corresponding to the control device 430 illustrated in FIG. 9 to be discussed later).

The arm unit 512 includes multiple joint units 513*a*, 513*b*, and 513*c*, multiple links 514*a* and 514*b* joined by the joint units 513*a* and 513*b*, and an imaging unit 515 joined to the front edge of the arm unit 512 by the joint unit 513*c*. The joint units 513*a* to 513*c* are provided with an actuator 300 illustrated in FIG. 10 to be discussed later, and the joint units 513*a* to 513*c* are configured to be rotatable about a certain rotary shaft according to the driving of the actuator 300. By controlling the driving of the actuator 300 with the above control device, the rotational angle of each of the joint units 513*a* to 513*c* is controlled, and the driving of the arm unit 512 is controlled.

The motors 110 and 210 according to the first and second embodiments described above may be applied favorably as the motor of the actuator 300. Consequently, the actuator 300, or in other words, the joint units 513*a* to 513*c* may be made more compact, thereby making it possible to make the overall arm unit 512 more compact as well.

Note that FIG. 8 illustrates a simplified configuration of the arm unit 512 for the sake of simplicity, but in actuality, factors such as the numbers of the joint units 513*a* to 513*c* and the links 514*a* and 514*b*, their arrangement, and the directions of the drive shafts (rotary shafts) of the joint units 513*a* to 513*c*, may be set appropriately so that the arm unit 512 has the desired degrees of freedom. For example, the arm unit 512 preferably may be configured to have six or more degrees of freedom. As a result, it becomes possible to move the imaging unit 515 freely within the movable range of the arm unit 512.

The imaging unit 515 is an example of an observation unit for observing the surgical site of the patient 540, and is a device such as a camera capable of capturing a moving image and/or a still image of an imaging target, for example. Other examples of the observation unit include an endoscope or a microscope, for example. In this specification, a support arm apparatus in which such an observation unit that observes the surgical site of the patient 540 is provided on the front edge of the arm unit 512 is also called an observation device.

When performing surgery, as illustrated in FIG. 8, the position and the orientation of the arm unit 512 and the imaging unit 515 are controlled by the support arm apparatus 510 so that the imaging unit 515 provided on the front edge of the arm unit 512 captures an image of the surgical site of the patient 540. In the operating room, a display device 550 is installed at a position facing the surgeon 520, and an image of the surgical site captured by the imaging unit 515 is displayed on the display device 550. The surgeon 520 performs various treatments while observing the image of the surgical site displayed on the display device 550.

Note that the front edge unit provided on the front edge of the arm unit 512 is not limited to an observation unit such as the imaging unit 515, and may also be any of various types of medical tools. Such medical tools may include various operating tools, such as forceps and retractors, for example, besides the observation unit discussed above. In the past, since these medical tools were manipulated manually, surgery required a large number of medical staff, but by having the support arm apparatus 510 manipulate these medical tools, it becomes possible to perform surgery with fewer people.

The above thus describes a state of surgery using the support arm apparatus 510 with reference to FIG. 8. In the example illustrated in FIG. 8, the support arm apparatus 510 is used for surgery, but in cases in which a unit used for examination, such as an endoscope, is provided as the front edge unit, for example, the support arm apparatus 510 may also be used for the purpose of examination.

Herein, in the support arm apparatus 510 for medical use as described above, the arm unit 512 is taken to be positioned near the surgical site during surgery or examination. Consequently, if the configuration of the arm unit 512 is large, there is a possibility that the workspace of the surgeon 520 may become limited, and performing treatment smoothly may become difficult. Also, as illustrated in the drawing, in the case in which the surgeon 520 performs surgery while referring to an image on the display device 550, since the arm unit 512 may be positioned in between the surgeon 520 and the display device 550, if the configuration of the arm unit 512 is large, there is a risk that the visual field of the surgeon 520 observing the display device 550 may become obstructed, and the work of the surgeon 520 may be inhibited.

In this way, in order to perform surgery or examination more smoothly, there is demand for the arm unit 512 of the support arm apparatus 510 for medical use to be more compact. According to this application example, by providing each of the joint units 513*a* to 513*c* with the actuator 300 having the motor 110 or 210 according to the first or second embodiment installed onboard, the arm unit 512 may be configured more compactly, thereby making it possible to meet the above demand.

Hereinafter, a configuration of a support arm apparatus according to the present application example will be described in further detail.

(5-2. Overall Configuration of Support Arm Apparatus)

Figure 9:
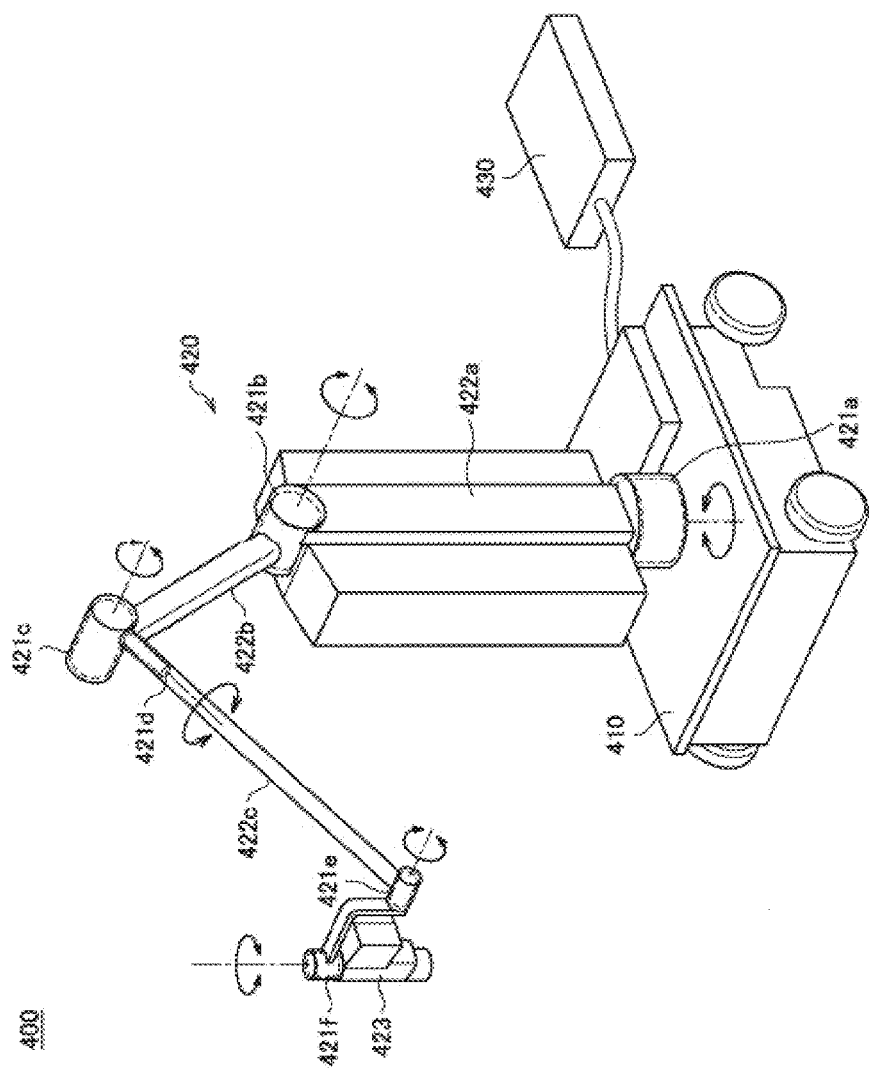
FIG. 9 is a diagram illustrating an example of an overall configuration of a support arm apparatus to which a motor according to a first or a second embodiment may be applied.

An overall configuration of a support arm apparatus to which the motors 110 and 210 according to the first and second embodiments may be applied will be described with reference to FIG. 9. FIG. 9 is a diagram illustrating an example of an overall configuration of a support arm apparatus to which the motors 110 and 210 according to the first and second embodiments may be applied.

Referring to FIG. 9, the support arm apparatus 400 is equipped with a base unit 410, an arm unit 420, and a control device 430. Similarly to the support arm apparatus 510 illustrated in FIG. 8 discussed above, the support arm apparatus 400 is a medical support arm apparatus that may be applied favorably to procedures such as surgeries and examinations.

The base unit 410 is the base of the support arm apparatus 400, and the arm unit 420 extends from the base unit 410. The base unit 410 is provided with casters, and thus the support arm apparatus 400 contacts the floor through the casters, and is movable across the floor by the casters.

The arm unit 420 includes a plurality of joint units 421*a* to 421*f*, a plurality of links 422*a* to 422*c* that are connected with one another by the joint units 421*a* to 421*f*, and an imaging unit 423 installed at the front edge of the arm unit 420.

The links 422a to 422c are rod-like members, one end of the link 422a is connected with the base unit 410 through the joint unit 421a, the other end of the link 422a is connected with one end of the link 422b through the joint unit 421b, and the other end of the link 422b is connected with one end of the link 422c through the joint units 421c and 421d. Further, the imaging unit 423 is connected to the front edge of the arm unit 420, that is, the other end of the link 422c through the joint units 421e and 421f. As described above, the arm shape extending from the base unit 410 is configured such that the base unit 410 serves as a support point, and the ends of the plurality of links 422a to 422c are connected with one another through the joint units 421a to 421f.

The imaging unit 423 is an example of an observation unit for observing a surgical site, and is a device such as a camera capable of capturing a moving image and/or a still image of an imaging target, for example. The imaging unit 423 corresponds to the imaging unit 515 illustrated in FIG. 8 discussed above. An image of the patient's surgical site captured by the imaging unit 423 is displayed on a display device (not illustrated) provided in the operating room, for example, and the surgeon performs surgery while observing the image of the patient's surgical site displayed on the display device. In this way, the support arm apparatus 400 may be an observation apparatus 400 in which an observation unit is attached to the front edge of the arm unit 420. As discussed earlier, devices such as an endoscope or a microscope, for example, may also be provided as the observation unit.

However, the front edge unit provided on the front edge of the arm unit 420 is not limited to an observation unit, and any of various treatment tools, such as forceps or a retractor, for example, may also be connected to the front edge of the arm unit 420.

The joint units 521a to 521f are provided with an actuator 300 illustrated in FIG. 10 to be discussed later, and the joint units 521a to 521f are configured to be rotatable about a certain rotary shaft according to the driving of the actuator 300. The driving of the actuator 300 is controlled by the control device 430. By respectively controlling the driving of the actuator 300 in each of the joint units 421a to 421f, driving of the arm unit 420 is controlled so as to extend or contract (fold up) the arm unit 420, for example.

In this application example, the motor 110 or 210 according to the first or second embodiment described earlier may be installed onboard the actuator 300 of each of the joint units 421a to 421f. Consequently, the actuator 300, or in other words, the joint units 421a to 421f may be made more compact, thereby making it possible to make the overall arm unit 420 more compact as well. Note that a configuration of the actuator 300 will be described in detail in (5-3. Configuration of actuator) below.

Note that in the example illustrated in the drawing, the support arm apparatus 400 includes six joint units 421a to 421f, and six degrees of freedom are realized with respect to the driving of the arm unit 420. By configuring the arm unit 420 to have six degrees of freedom, the imaging unit 423 may be moved freely within the movable range of the arm unit 420. Consequently, it becomes possible to use the imaging unit 423 to image the surgical site from a variety of angles and distances. However, the configuration of the arm unit 420 is not limited to the example illustrated in the drawing, and factors such as the numbers of the joint units 421a to 421f and the links 422a to 422c, their arrangement, and the directions of the drive shafts of the joint units 421a to 421f, may be set appropriately so that the arm unit 420 has the desired degrees of freedom. However, in consideration of freedom in the position and the orientation of the imaging unit 423, the arm unit 420 preferably may be configured to have six or more degrees of freedom.

The control device 430 is made up of a processor, such as a central processing unit (CPU) or a digital signal processor (DSP), for example, or a microcontroller with these processors installed onboard. By executing signal processing according to a certain program, the control device 430 controls the driving of the support arm apparatus 400.

The method of controlling the support arm apparatus 400 is not particularly limited, and the operation of the support arm apparatus 400 may be controlled by any of various known control methods, such as position control or force control. In the case of controlling the support arm apparatus 400 by position control, an input device such as a controller for operating the arm unit 420 may be provided. In the case of controlling the arm unit 420 by force control, the operation of the arm unit 420 may be controlled so that a user touches and operates the arm unit 420 directly, for example, and in response to an operation attempting to move the arm unit 420, the arm unit 420 moves in the direction of the force applied to the arm unit 420. Note that since any of various known methods may be used as the specific methods of controlling the support arm apparatus 400 by position control or force control, a detailed description is omitted herein.

Note that in the example illustrated in the drawing, the control device 430 is connected to the base unit 410 via a cable, but a component such as a control board having functions similar to the control device 430 may also be provided internally inside the base unit 410.

The above thus references FIG. 9 to describe an overall configuration of the support arm apparatus 400 to which the motors 110 and 210 according to the first and second embodiments may be applied.

(5-3. Configuration of Actuator)

A configuration of the actuator provided in each of the joint units 421a to 421f of the support arm apparatus 400 illustrated in FIG. 9 will be described with reference to FIG. 10. FIG. 10 is an exploded perspective view illustrating an example configuration of an actuator provided in each of the joint units 421a to 421f of the support arm apparatus 400 illustrated in FIG. 9.

Figure 10:
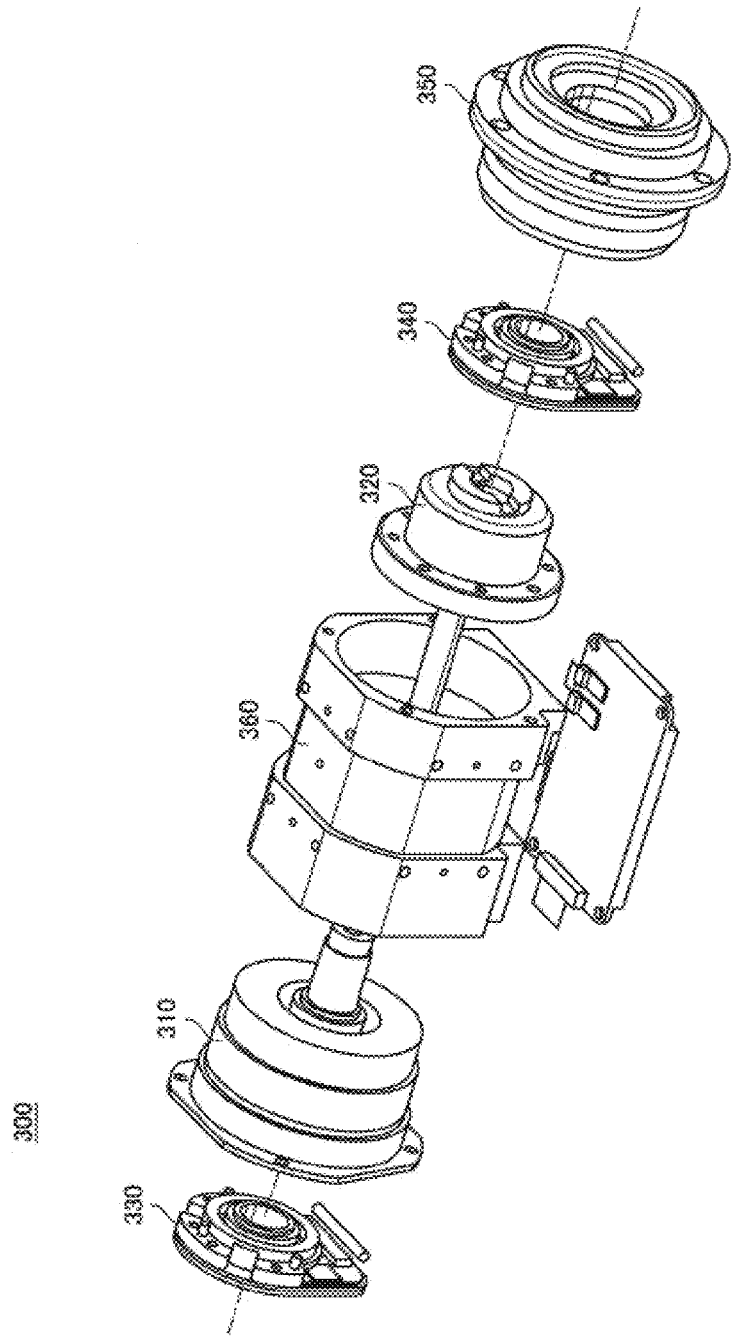
FIG. 10 is an exploded perspective view illustrating an example configuration of an actuator provided in each joint unit of the support arm apparatus illustrated in FIG. 9.

Referring to FIG. 10, the actuator 300 is equipped with a motor 310, a reduction gear 320, an input shaft encoder 330, an output shaft encoder 340, an output shaft 350, and a housing 360. In the actuator 300, the rotation of the rotary shaft of the motor 310 is reduced by the reduction gear 320 at a certain reduction ratio, and transmitted to other downstream members via the output shaft 350. As a result, the other members are driven.

The housing 360 has an approximately cylindrical shape, in which the respective components are housed internally. In a state in which each of the structural members is housed inside the housing 360, the actuator 300 is built into each of the joint units 421a to 421f of the support arm apparatus 400 discussed above.

The motor 310 is a driving mechanism that, when given a certain command value (current value), causes a rotary axis to rotate at a rotational velocity corresponding to the command value, and thereby produces driving force. In this application example, the motor 110 or 210 according to the first or second embodiment discussed earlier is used as the motor 310. Consequently, it is not necessary to provide an insulating structure such as an insulator between the rotary shaft or the outer covering of the motor 310 and other adjacent members, and thus it becomes possible to make the actuator 300 more compact.

The reduction gear 320 is joined to the rotary shaft of the motor 310. The reduction gear 320 reduces by a certain reduction ratio the rotational velocity of the rotary shaft of the joined motor 310 (in other words, the rotational velocity of the input shaft), and transmits to the output shaft 350. In this application example, the configuration of the reduction gear 320 is not limited to a specific configuration, and any of various known reduction gears may be used as the reduction gear 320. However, for the reduction gear 320, it is preferable to use one capable of accurately setting the reduction ratio, such as a Harmonic Drive (registered trademark), for example. In addition, the reduction ratio of the reduction gear 320 may be set appropriately according to the application of the actuator 300. For example, in the case of applying the actuator 300 to the joint units 421a to 421f of the support arm apparatus 400 as in the present application example, a reduction gear 320 having a reduction ratio of approximately 1:100 preferably may be used.

The input shaft encoder 330 detects the rotational angle of the input shaft (that is, the rotational angle of the motor 310). The output shaft encoder 340 detects the rotational angle of the output shaft 350. The configuration of the input shaft encoder 330 and the output shaft encoder 340 is not limited, and any of various known types of rotary encoders, such as magnetic encoders or optical encoders, for example, may be used as the input shaft encoder 330 and the output shaft encoder 340.

The above thus references FIG. 10 to describe a configuration of the actuator 300 to which the motors 110 and 210 according to the first and second embodiments may be applied. Note that the actuator 300 additionally may be provided with other configuration elements besides the illustrated configuration elements. For example, the actuator 300 additionally may be provided with various types of members that may be included in a typical actuator, such as a driver circuit (driver integrated circuit (IC)) that induces rotational driving in the motor 310 by supplying a current to the motor 310, or a torque sensor that detects the torque acting on the output shaft 350. Particularly, in the case in which the operation of the support arm apparatus 400 is controlled by force control, a torque sensor preferably may be provided in the actuator 300 to detect the force acting on the arm unit 420.

6. Supplement

The preferred embodiments of the present disclosure have been described above with reference to the accompanying drawings, whilst the present disclosure is not limited to the above examples, of course. A person skilled in the art may find various alterations and modifications within the scope of the appended claims, and it should be understood that they will naturally come under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification. Additionally, the present technology may also be configured as below.

(1)
A motor, wherein an electrically active part is provided with an insulating structure so that insulating properties between the electrically active part and one or more conductors near the electrically active part satisfy a certain safety standard regarding medical electrical equipment.

(2)
The motor according to (1), wherein
the insulating structure is a structure in which an insulator satisfying the certain safety standard is provided between the electrically active part and the one or more conductors.

(3)
The motor according to (1) or (2), wherein
the insulating structure is a structure in which a clearance distance and a creepage distance satisfying the certain safety standard are provided between the electrically active part and the one or more conductors.

(4)
The motor according to any one of (1) to (3), wherein
the certain safety standard is IEC 060601-1.

(5)
The motor according to any one of (1) to (4), wherein
the motor is a coreless brushless motor not provided with a stator core, and
the electrically active part provided with the insulating structure is a coil.

(6)
The motor according to any one of (1) to (4), wherein
the motor is a brushless motor including a stator core, and
the electrically active part provided with the insulating structure is a coil.

(7)
An actuator, including:
a motor in which an electrically active part is provided with an insulating structure so that insulating properties between the electrically active part and one or more conductors near the electrically active part satisfy a certain safety standard regarding medical electrical equipment, wherein
the actuator is used in a drive mechanism of medical electrical equipment.

(8)
A medical support arm apparatus, including:
an arm unit made up of a plurality of joint units; and
a medical tool provided on a front edge of the arm unit, wherein
in a motor of an actuator provided in the joint unit, an electrically active part is provided with an insulating structure so that insulating properties between the electrically active part and one or more conductors near the electrically active part satisfy a certain safety standard regarding medical electrical equipment.

(9)
The medical support arm apparatus according to (8), wherein
the joint unit is made up of a movable mechanism including a stationary part and a movable part, and
the motor is attached between the stationary part and the movable part without an additional interposing insulating structure.

(10)
The medical support arm apparatus according to (8) or (9), wherein
the medical tool provided on the front edge of the arm unit is an observation unit for observing a surgical site.

(11)
The medical support arm apparatus according to any one of (8) to (10), wherein
driving of the actuator provided in the joint unit is controlled by force control.

REFERENCE SIGNS LIST 10, 60, 70 movable mechanism
110, 610, 710 motor 120, 620, 720 stationary part
130, 630, 730 movable part
111, 211 drive shaft
112, 212 magnet
113, 213 coil
114 back yoke
115, 215 housing
116, 216 insulator
214 stator core
300 actuator
310 motor
320 reduction gear
330 input shaft encoder
340 output shaft encoder
350 output shaft
360 housing
400, 510 support arm apparatus (observation apparatus)
410, 511 base unit
420, 512 arm unit
421a to 421f, 513a to 513c joint unit
423, 515 imaging unit
430 control device
640, 740 insulator

The invention claimed is:

1. A medical support arm apparatus, comprising:
    a multi joint arm that comprises a plurality of joints;
    a medical tool supported on a distal end of the multi joint arm; and
    an actuator provided in at least one joint of the plurality of the joints, wherein
        the actuator includes a motor,
        the motor includes an electrically active part, an insulating structure for the electrically active part, and at least one conductor in proximity to the electrically active part,
        the insulating structure is provided with a clearance distance between the electrically active part and a first conductor of the at least one conductor and a creepage distance between the electrically active part and a second conductor of the at least one conductor, and
        the clearance distance and the creepage distance are stipulated by a safety standard associated with a medical electrical equipment.

2. The medical support arm apparatus according to claim 1, wherein
    the at least one joint of the plurality of the joints is made of a movable mechanism including a stationary part and a movable part, and
    the motor is attached between the stationary part and the movable part without the insulating structure.

3. The medical support arm apparatus according to claim 1, wherein the medical tool on the distal end of the multi joint arm is an observation unit for observation of a surgical site.

4. The medical support arm apparatus according to claim 1, wherein the actuator further includes a reduction gear and an encoder.

5. The medical support arm apparatus according to claim 1, wherein the actuator further includes a torque sensor.

6. The medical support arm apparatus according to claim 1, wherein the actuator is configured to move based on an applied force.

7. The medical support arm apparatus according to claim 1, wherein the safety standard is IEC 060601-1.

8. The medical support arm apparatus according to claim 1, wherein the insulating structure has an insulator.

9. The medical support arm apparatus according to claim 1, wherein
    the motor is a coreless brushless motor without a stator core, and
    the electrically active part is a coil.

10. The medical support arm apparatus according to claim 1, wherein
    the motor is a brushless motor including a stator core, and
    the electrically active part is a coil.

11. A motor, comprising:
    an electrically active part;
    an insulating structure for the electrically active part; and
    at least one conductor in proximity to the electrically active part, wherein
        the insulating structure is provided with a clearance distance between the electrically active part and a first conductor of the at least one conductor and a creepage distance between the electrically active part and a second conductor of the at least one conductor, and
        the clearance distance and the creepage distance are stipulated by a safety standard associated with a medical electrical equipment.

12. The motor according to claim 11, wherein the safety standard is IEC 060601-1.

13. The motor according to claim 11, wherein the insulating structure has an insulator.

14. The motor according to claim 11, wherein
    the motor is a coreless brushless motor without a stator core, and
    the electrically active part is a coil.

15. The motor according to claim 11, wherein
    the motor is a brushless motor including a stator core, and
    the electrically active part is a coil.

* * * * *